United States Patent
Zhdanov

(10) Patent No.: US 6,253,100 B1
(45) Date of Patent: Jun. 26, 2001

(54) METHOD OF BROAD BAND ELECTROMAGNETIC HOLOGRAPHIC IMAGING

(75) Inventor: Michael S. Zhdanov, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/214,217
(22) PCT Filed: Jun. 26, 1997
(86) PCT No.: PCT/US97/11217
§ 371 Date: Dec. 23, 1998
§ 102(e) Date: Dec. 23, 1998
(87) PCT Pub. No.: WO97/49329
PCT Pub. Date: Dec. 31, 1997

Related U.S. Application Data
(60) Provisional application No. 60/020,622, filed on Jun. 26, 1996.

(51) Int. Cl.[7] .............................. A61B 5/00; G01R 27/00
(52) U.S. Cl. ......................... 600/407; 600/547; 324/693
(58) Field of Search .................................. 600/407, 547, 600/430, 476; 324/600, 693; 73/603; 342/22; 356/347

(56) References Cited

U.S. PATENT DOCUMENTS

| | | |
|---|---|---|
| 3,887,923 * | 6/1975 | Hendrix . |
| 4,852,575 | 8/1989 | Nikoonahad . |
| 4,945,239 | 7/1990 | Wist et al. . |
| 4,948,974 | 8/1990 | Nelson et al. . |
| 5,072,128 | 12/1991 | Hayano et al. . |
| 5,303,710 | 4/1994 | Bashkansky et al. . |
| 5,327,139 * | 7/1994 | Johnson ................. 342/22 |
| 5,373,443 | 12/1994 | Lee et al. . |
| 5,413,098 | 5/1995 | Benaron . |
| 5,418,797 | 5/1995 | Bashkansky et al. . |
| 5,435,312 * | 7/1995 | Spivey et al. . |
| 5,476,108 | 12/1995 | Dominguez et al. . |
| 5,503,150 | 4/1996 | Evans . |
| 5,592,170 * | 1/1997 | Price et al. ............. 342/22 |
| 5,606,969 | 3/1997 | Butler et al. . |
| 5,673,050 * | 9/1997 | Moussally et al. .......... 342/22 |
| 5,807,257 * | 9/1998 | Bridges ................. 600/430 |

* cited by examiner

Primary Examiner—Marvin M. Lateef
Assistant Examiner—Shawna J Shaw
(74) Attorney, Agent, or Firm—Knobbe, Martens, Olson & Bear, LLP

(57) ABSTRACT

A method of imaging an object, such as a diseased human heart or bone, in a nontransparent medium, such as the human body, involves placing an array of transmitters and receivers in operational association with the medium. The transmitters generate a harmonic (frequency domain) or pulse (time domain) primary electromagnetic field (EM) which propagates through the medium. The primary field interacts with the object to produce a scattered field, which is recorded by the receivers. The scattered EM field components measured by the receivers are applied as an artificial EM field to generate a backscattering EM field. Cross power spectra of the primary and backscattering fields (in the frequency domain) or cross correlation between these fields (in the time domain) produce a numerical reconstruction of an EM hologram. The desired properties of the medium, such as conductivity or dielectric permittivity, are then derived from this hologram.

8 Claims, 4 Drawing Sheets

METHOD OF BROAD BAND ELECTROMAGNETIC HOLOGRAPHIC IMAGING

This application claims the priority of U.S. Provisional Application Serial No. 60/020,622, filed Jun. 26, 1996, entitled "METHOD OF BROAD BAND ELECTROMAGNETIC HOLOGRAPHIC IMAGING."

TECHNICAL FIELD

This invention relates to three dimensional ("holographic") imaging. It is specifically directed to the electromagnetic (EM) imaging of an object within a nontransparent medium. It provides methodology and apparatus for conducting nondestructive and/or non-invasive inspections, utilizing broad band electromagnetic signals.

BACKGROUND ART

Conventional optical holography constructs a volume (three dimensional) image of an object by displaying the amplitude and the phase structure of a wavefront of light. A reference wave of light is relied upon to facilitate the recording of both the amplitude and the phase condition of the object light by means of photographic emulsion. This reference wave is coherent with the object light and interferes with it, producing diffraction patterns which form an optical hologram on the photographic emulsion. To generate a volume image, this optical hologram need merely be illuminated with a reference light wave. The resulting diffraction pattern wave (as scattered by the emulsion) is identical to the original wavefront of light scattered by the object, and therefore reproduces the volume image of the object.

U.S. Pat. No. 3,887,923 to Hendrix discloses an application of the principles of optical holography within the radio-frequency domain. The '923 patent discloses a passive radio direction finder which monitors the amplitude and phase of radio-frequency wave fronts across an aperture. An array of antennas sample the phase of incoming wave fronts. Each antenna is associated with a mixer, and one of the antennas provides a mixer reference signal for an input to each mixer. The signals are processed through an analog-to-digital converter and a computer programmed rapidly to execute Fourier transforms, eventually to produce a numerical reconstruction of the radio frequency hologram.

U.S. Pat. No. 5,299,033 to Leith, et al discloses a method whereby an image of an object embedded in a diffusing medium is formed by propagating a coherent light pulse through the diffusing medium and applying a reference pulse to gate precisely the first emerging light transmitted through the diffusing medium. To produce an image, it is necessary for the diffusing medium to be transparent, because the method relies upon optical light.

There have been several attempts to develop an imaging method, utilizing a low frequency electromagnetic (EM) field, especially as applied to the solution of geophysical problems. K. H. Lee and G. Xie, in both U.S. Pat. No. 5,373,443 and the article, "A new approach to imaging with low-frequency electromagnetic fields," Geophysics, volume 58, pages 780–796 (1993), describe a method for imaging electrical conductivity with low-frequency electromagnetic fields, using wavefield transforms and ray tomography. This work has recognized a relationship between low frequency diffusion EM field equations and wave equations, but practical applications of this method have been directed to defining interfaces, rather than three dimensional imaging.

In the article entitled "Continuation of the transient electromagnetic field in the geoelectrical problems," Physics of the Earth (Izvestia Akademy Nauk—in Russian), No. 12, pages 60–69, 1981, the present inventor presented a mathematical transform, based upon the theory of Stratton-Chu integrals, of the field recorded on the earth's surface and scattered from a subsurface geological object downward to locate and image the object. Subsequently, the present inventor and M. A. Frenkel coauthored an article entitled "The solution of the inverse problems on the basis of the analytical continuation of the transient electromagnetic field in reverse time," J. Geomagn. Geolelectr., volume 35, pages 747–765 (1983), which developed this method and introduced an imaging concept based upon downward extrapolation of an EM field in reverse time (electromagnetic migration).

The inventor has further coauthored the articles: "Resistivity Imaging by Time Domain Electromagnetic Migration (TDEMM)" (with P. Traynin and O. Portniaguine), Exploration Geophysics, volume 26, pages 186–194 (1995), reporting work which tested the imaging concept using controlled-source electromagnetic data, with limited success for two-dimensional models only, and "Underground Imaging by Frequency Domain Electromagnetic Migration," (with P. Traynin and J. R. Booker), Geophysics, volume 61, No. 3, pages 666–682 (1996), explaining application of the migration method to natural EM field geophysical data interpretation, but this study was limited to two-dimensional magnetotelluric problems.

These earlier efforts to develop a method for quickly interpreting geophysical EM data over two-dimensional geoelectrical structures have met with limited success. Moreover, they have not pointed towards a practically useful method for accomplishing broad band EM imaging of three-dimensional objects in nontransparent media. There remains a need for a method of imaging capable of providing the volume image of objects located in nontransparent media similar to images produced by optical or radio-wave holography. Such a method would be useful in geophysical exploration, in environmental study (for example, in searching for buried mines), for nondestructive detection of defects in metal and in medical applications (for example, in breast cancer or diseased bone diagnoses).

DISCLOSURE OF INVENTION

According to this invention, a broad band electromagnetic (EM) field may be utilized for imaging an object located in a nontransparent medium. Examples of a nontransparent medium are geophysical structures of the earth, animal (including human) bodies and substances generally which block transmissions from the high frequency range of the electromagnetic spectrum. Because this invention utilizes the lower frequency portions of the EM spectrum, useful images can be obtained under circumstances in which neither optical nor radio-frequency signals can propagate through the medium in which the image target is located. Lower frequency waves characteristically propagate deeper through any diffusing medium.

In practice, the EM transmitting/receiving system may be placed in operable association with the surface of the examined medium. "Operational association," in this context, means any location which facilitates propagation of a field through an examined medium from a transmitter to a receiver. Ordinarily, the transmitters and receivers are most conveniently positioned directly on the surface of the examined medium, but they can be positioned within the medium or, in some instances, inductor devices may be placed in the proximity of the medium. The transmitters and receivers may be either galvanic or inductive in construction. Transmitters and receivers of both types may be used in specific applications.

The transmitters generate a harmonic (frequency domain) or pulse (time domain) primary EM field which propagates through the medium containing the target object, and is recorded by the receivers. A reference signal is provided to measure relative phases in the frequency domain. The recorded amplitudes and phases of the electromagnetic field scattered by the object form a broad band EM hologram. The volume image of the object can be reconstructed by "illuminating" the broad band EM hologram with the reference signal. Unlike optical or radio-frequency holographic imaging techniques, which can yield a visible image optically, reconstruction in accordance with this invention is done numerically, using computer transformation techniques.

The present invention provides a new capability for imaging in nontransparent media with a broad band EM field. The EM transmitting/receiving system is generally placed on the surface of the examined medium. The transmitters generate either (or both) a harmonic (frequency domain) or pulse (time domain) primary EM field which propagates through the medium containing the object. The "scattered-by-the-object" EM field is recorded by the receivers. A central processing unit (CPU) is connected to collect the recorded amplitudes and phases of scattered-by-the-object electromagnetic field and to form a broad band EM hologram.

The method is ideally suited for applications which determine the distribution of electromagnetic parameters (such as conductivity or dielectric permittivity) distribution within a target object or substance with high accuracy and resolution. The desired properties, such as conductivity or dielectric permittivity, of the target are readily derived from the hologram. The measured EM field components in the receiver locations (amplitudes and phases in frequency domain or time signals in time domain) are conveniently selected as the boundary conditions of the EM field to generate numerically the backscattering EM field. Vector cross power spectra of the primary and backscattering fields produce a numerical reconstruction of a volume image of conductivity or dielectric permittivity distribution.

An imaging apparatus, capable of performing in real time in accordance with the method of this invention for broad band EM holographic imaging requires a relatively simple hardware arrangement and simple software.

Broadly, the invention comprises a method of imaging an object, such as a diseased human organ or bones, in a nontransparent medium, such as the human body. The method involves placing an array of transmitters and receivers in operational association with the medium. The transmitters generate a harmonic (frequency domain) and/or a pulse (time domain) primary EM field which propagates through the medium. The primary field interacts with the object to produce a scattered field, which is recorded by the receivers. The scattered EM field components measured by the receivers are applied as an artificial EM field to generate a backscattering EM field. This backscattered field may be obtained empirically or by numerical calculation. Cross power spectra of the primary and backscattering fields (in frequency domain) or cross correlation between these fields (in time domain) produce a numerical reconstruction of an EM hologram. The desired properties of the medium, such as conductivity or dielectric permittivity, may then be derived from this hologram.

More specifically, an anomalous target located in a nontransparent examined medium may be located and characterized through a method comprising the steps of:

a. placing an electromagnetic transmitter source in transmission contact with the examined medium;

b. placing electromagnetic receivers at various receiving positions with respect to the examined medium, spaced from the transmitter source;

c. operating the transmitter source to generate a broad band electromagnetic field comprising an harmonic (frequency domain) and/or pulse (time domain) electromagnetic field, whereby the generated electromagnetic field propagates through the examined medium to interact with the target, resulting in a scattered electromagnetic field;

d. measuring the scattered electromagnetic field with the receivers;

e. obtaining a background field $\{E^b, H^b\}$ representative of the examined medium without the presence of the anomalous target (often referred to as the "background" medium);

f. obtaining a backscattering anomalous field $\{E^{as}, H^{as}\}$ equivalent to that obtainable by illuminating the background medium with the scattered electromagnetic field transmitted from the positions of the receivers; and g. producing a broad band holographic image of the anomalous target by calculating cross power spectra of the background and the backscattering fields (frequency domain) and/or cross correlation functions between the background and the backscattering fields (time domain).

Ideally, the scattered electromagnetic field measured by step d. is input to a computer, and the computer is operated to: (1) analyze the scattered electromagnetic field; (2) numerically simulate illumination of the background medium by the original transmitter source; (3) compute the backscattering anomalous field $\{E^{as}, H^{as}\}$ by simulating illumination of the background medium from the locations of the receivers with electric and magnetic currents equivalent to those of the scattered electromagnetic field; and (4) constructing a volume image of electrical conductivity and/or dielectric permittivity by calculating cross power spectra of the background and backscattering fields.

As applied to imaging an anomalous region located within an organism, such as the bones, liver or heart of a human being, the method may comprise the steps of:

a. placing an electromagnetic transmitter source on the surface of the organism (or optionally, in the case of inductor devices, in the proximity of the organism);

b. placing electromagnetic receivers at various positions on the surface of the organism (or optionally, in the case of inductor devices, in the proximity of the organism), spaced from the transmitter source;

c. operating the transmitter source to generate a broad band electromagnetic field comprising an harmonic (frequency domain) and/or pulse (time domain) electromagnetic field, whereby the generated electromagnetic field propagates through the organism to interact with the anomalous region, resulting in a scattered electromagnetic field;

d. measuring the scattered electromagnetic field with the receivers;

e. obtaining a background field $\{E^b, H^b\}$ representative of the organism without the presence of the anomalous region (often referred to as a "reference" organism, equivalent to a "background medium");

f. obtaining a backscattering anomalous field $\{E^{as}, H^{as}\}$ equivalent to that obtained by illuminating the reference organism by transmitting the scattered electromagnetic field from the positions of the receivers; and g. producing a broad band holographic image of the anomalous region by calculating cross power spectra of the background and the backscattering fields or cross correlation functions between the background and the backscattering fields.

BRIEF DESCRIPTION OF DRAWINGS

In the drawings, which illustrate what is currently regarded as the best mode for carrying out the invention.

MODES FOR CARRYING OUT THE INVENTION

Figure 1:
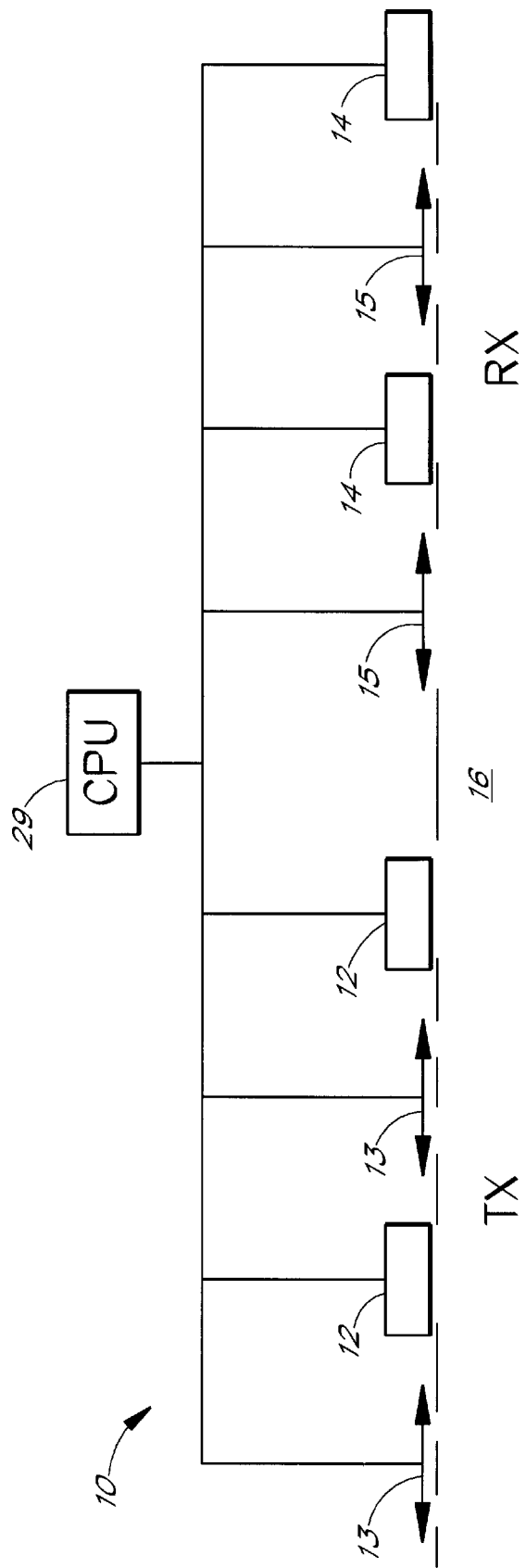
FIG. 1 illustrates an EM transmitting/receiving system placed on the surface of an examined medium in accordance with this invention.

A presently preferred approach to broad band EM holography is illustrated by FIG. 1. As illustrated, the imaging system 10 consists of induction 12 or galvanic 13 EM field transmitters and induction 14 or galvanic 15 EM field receivers placed on the surface of the examined medium 16 (FIG. 1). The array of receivers 14, 15 may either be one-dimensional (as shown) or two-dimensional (typically, distributed in a grid pattern across the surface of observation). Transmitters 12, 13 (or a single transmitter) can be located arbitrarily on the surface of the examined medium 16.

Figure 3:
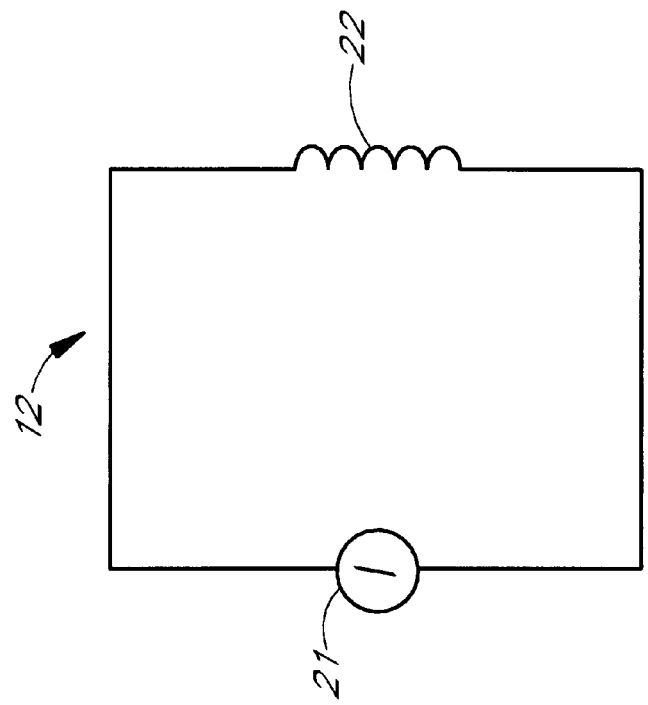
FIG. 3 is a simplified diagram of an induction transmitter useful in the system of FIG. 1.
Figure 2:
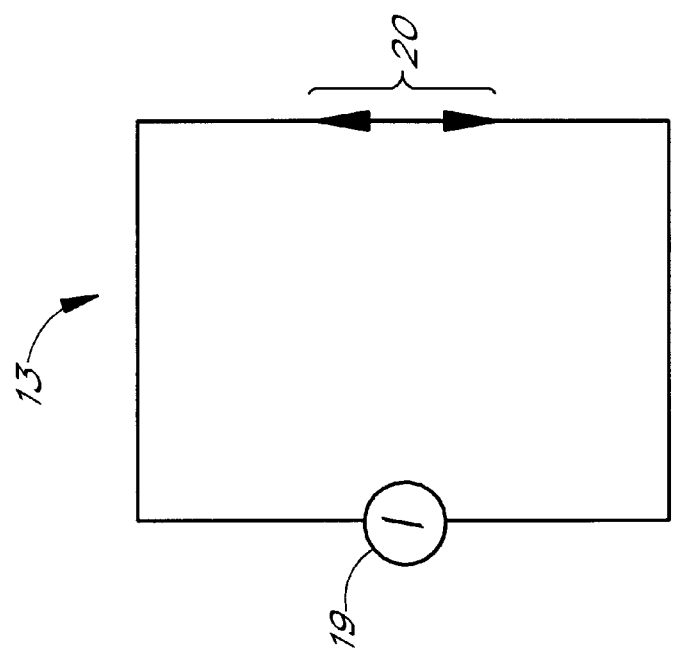
FIG. 2 is a simplified diagram of a galvanic transmitter useful in the system of FIG. 1.
Figure 5:
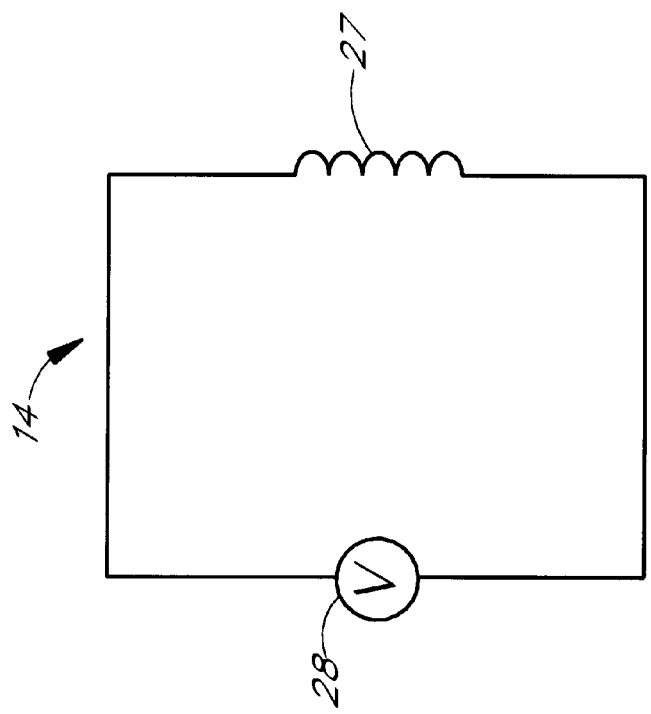
FIG. 5 is a simplified diagram of an induction receiver useful in the system of FIG. 1.
Figure 4:
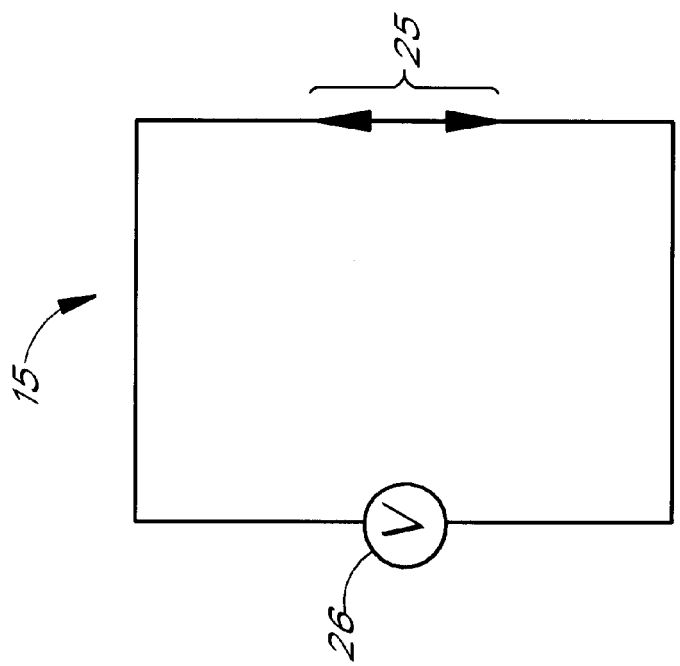
FIG. 4 is a simplified diagram of a galvanic receiver useful in the system of FIG. 1.

The galvanic transmitter 13 (FIG. 2) consists of the transient current source 19 connected across the pair of current electrodes 20. The induction transmitter 12 (FIG. 3) consists of the transient current source 21 connected across a solenoid coil 22. The galvanic receiver 15 (FIG. 4) consists of a pair of receiver electrodes 25 connected across the voltmeter 26. The induction receiver 14 (FIG. 5) consists of a solenoid coil 27 connected across the voltmeter 28. In use, galvanic devices are positioned in direct contact with the examined medium, but induction devices are operable from positions in the proximity of, but not necessarily in contact with, the examined medium.

Figure 6:
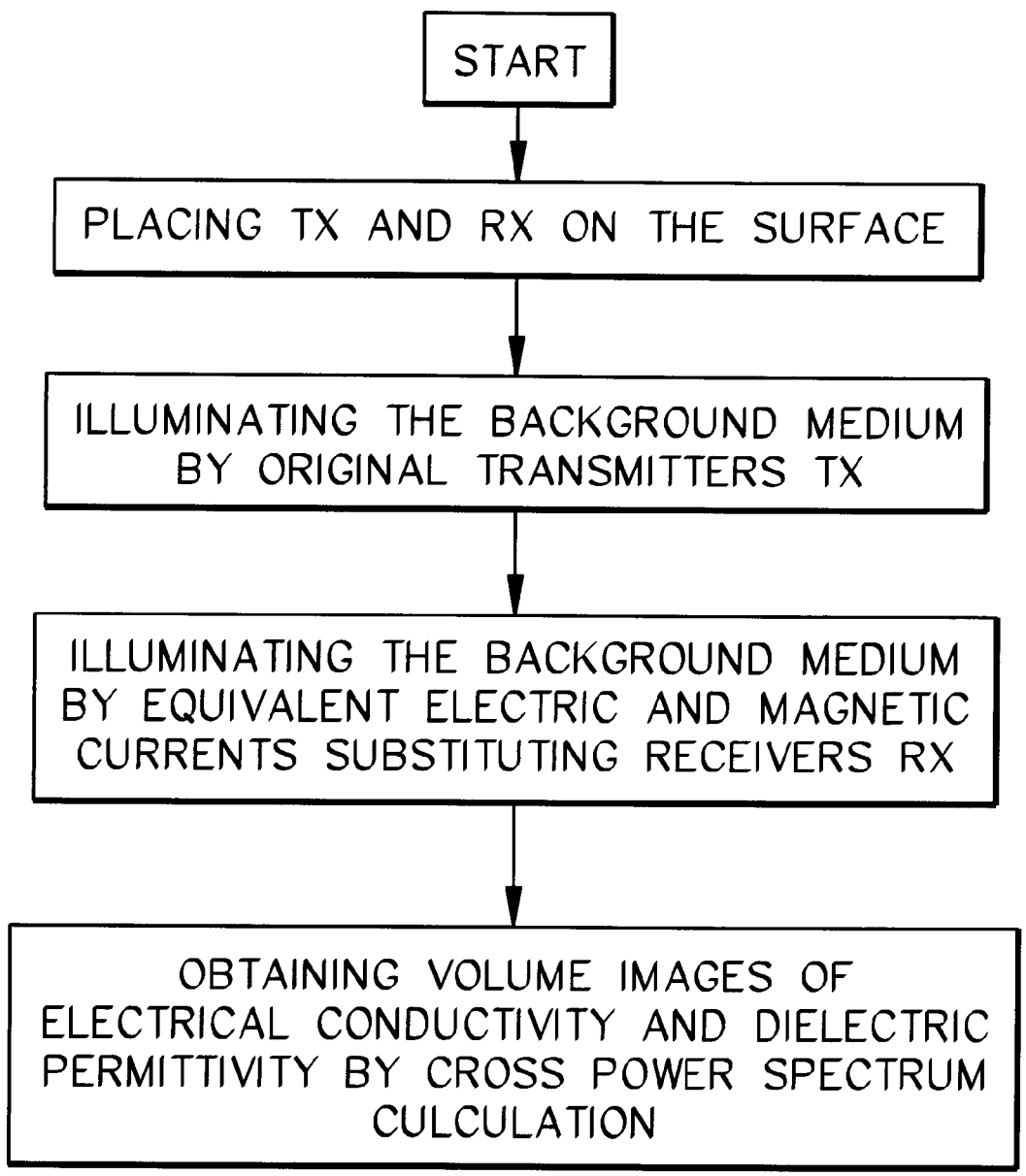
FIG. 6 is a flow chart illustrating a method of holographic imaging by the broad band EM system of FIG. 1.

The central processing unit 29 (FIG. 1) operates the broad band EM holographic imaging system, as it is schematically shown by FIG. 6. The incoming EM field generated by a transmitter (or, as illustrated, an array TX of transmitters) is received by an array of receivers RX, and is recorded by the central processing unit 29. In the output of the receiver array shown in FIG. 1, the EM field measurements are inherently reduced to numerical values. It is thus expedient to proceed with a numerical reconstruction of the volume image.

EXAMPLE 1

The following explanation of the principles of broad band EM holographic imaging reconstruction is offered to assist those skilled in the art to practice the invention. It is not intended thereby to limit the scope of the invention to any particular theory of operation or to any field of application.

A three dimensional inhomogeneous medium, with a known background complex conductivity, $\sigma_b$, contains a local inhomogeneous object D with an arbitrarily varying complex conductivity $\sigma = \sigma_b + \sigma_a$. The location of D and its anomalous conductivity $\sigma_a$, are unknown. The examined medium is considered to be non-magnetic, and hence $\mu = \mu_0 = 4\pi \times 10^{-7}$ H/m, where $\mu$ is the magnetic permeability and $\mu_0$ is the free-space magnetic permeability. The model is excited by an EM field generated by a given system of sources (transmitters TX) with an electric current density $j^e$. This field is time harmonic as $e^{-i\omega t}$ and is observed by the system of receivers RX located on the surface S of the examined medium. Complex conductivity includes the effect of displacement currents: $\sigma = \sigma - i\omega\epsilon$, where $\sigma$ and $\epsilon$, are electrical conductivity and dielectric permittivity. The total EM field observed in this model can be represented as a sum of background (normal) field $\{E^b, H^b\}$ generated by the given system of transmitters in the model with the background conductivity distribution, and an anomalous field $\{E^a, H^a\}$, due to an inhomogeneity $\sigma_a$ (r):

$$E = E^b + E^a, \quad H = H^b + H^a \qquad (1)$$

where r is the radius vector of the observation point.

To generate the volume image of the object within the inhomogeneous medium, the same transmitter/receiver system is re-deployed in the same spatial configuration as used for the receiving mode of operation, on the surface of the medium with the conductivity equal to the background conductivity $\sigma_b$ (background medium). The receivers are operated as (or replaced by) auxiliary transmitters which generate electric $j_S^e$ and magnetic $j_S^m$ currents equivalent to those evaluated from the anomalous field previously recorded by the receivers, located on the surface S:

$$j_S^e = -n \times H^{a*},$$
$$J_S^m = n \times E^{a*}, \qquad (2)$$

where n is the unit vector of normal to S pointing outward the examining medium, and * indicates a complex conjugate value.

A typical imaging process of the invention thus comprises:

1. Illuminating the background medium by a selected system of transmitters (background field $\{E^b, H^b\}$ generation).

2. Illuminating the background medium by artificial transmitters located in the positions of the receivers and operated in response to equivalent (fictitious) electric $j_S^e$ and magnetic $J_S^m$ currents, determined by formulae (2) (backscattering anomalous field $\{E^{as}, H^{as}\}$ generation).

3. Producing a broad band holographic image by calculating cross power spectra of the background and backscattering fields.

Referring to FIGS. 1 and 6, the operation of imaging system 10 can be summarized as follows: An electromagnetic signal is generated by transmitters 12, 13, and is recorded by receivers 14, 15, placed on the surface of an examined medium, (for example, the earth or the body of a human being). The CPU system 29 analyzes the recorded field and fulfills the following numerical processes:

(1) It numerically simulates illumination of the background medium by the original system of transmitters TX.

(2) It computes the backscattering anomalous field $\{E^{as}, H^{as}\}$, simulating illumination of the background medium by equivalent electric and magnetic currents, substituting the receivers RX.

(3) It constructs the volume images of electrical conductivity and dielectric permittivity by calculating cross power spectra of the background and backscattering fields.

EXAMPLE 2

The image generating method of the present invention solves the minimum energy flow problem for the residual field $\{E^{66}, H^{66}\}$ computed as the difference between the observed field $\{E_{obs}, H_{obs}\}$ and numerically calculated (predicted) field $\{E_{pr}, H_{pr}\}$ for a constructed image.

The energy flow of the residual electromagnetic field can be calculated using the complex Poynting vector P, introduced by the formula:

$$P = 1/2 E^{66} \times H^{\Delta *}. \quad (3)$$

which is known to be a non-negative function.

The measure $\Phi$ of the difference between the observed and predicted fields can be introduced as the energy flow of the residual field through the surfaces of observations, integrated over the frequency $\omega$:

The theoretical predicted fields $E_{pr}(r,\omega)$, $H_{pr}(r,\omega)$ depend on the sum of the background $\sigma_b(r)$ and anomalous conductivity distribution $\sigma_a(r)$ in the examined $$\Phi = Re \int_{106} \int \int_S P \cdot n dS d\omega = 1/2 Re \int_{106} \int \int_S [E^{66}(r,\omega) \times H^{66\,*}(r,\omega)] \cdot n dS d\omega \quad (4)$$

medium, and, therefore, the residual field energy flow $\phi$ is a function of $[\sigma_b(r) + \sigma_a(r)]$:

$$\phi = \phi[\sigma_b + \sigma_a]. \quad (5)$$

It can be expressed approximately as:

$$\phi[\sigma_b + \sigma_a] \approx \phi(\sigma_b) + \delta\phi(\sigma_b, \sigma_a) \quad (6)$$

where $\delta\phi(\sigma_b, \sigma_a)$ is a gradient of the residual field energy flow. It is a linear function of anomalous conductivity and is computed by the formula:

$$\delta\phi(\sigma_b, \sigma_a) =$$

$$-1/2 Re \int \int \int_D \int_{106} \sigma_a(r') \int \int_S n \cdot \{E^{a*}(r,\omega) \times \hat{G}_H^b(r|r',\omega) - H^{a*}(r,\omega) \times \hat{G}_E^b(r|r',\omega)\} dS \cdot E^b(r',\omega) \, d\omega dv', \quad (7)$$

where v is the volume and dv is the elemental volume of integration and where $\hat{G}_E^b$ and $\hat{G}_H^b$ are electric and magnetic Green's tensors for the background conductivity $\sigma_b(r)$, whose vector components relate the electric and magnetic fields excited at the point r by an electric dipole source of unit intensity located at the point r' of the domain D.

It is known from the literature that the integral over the surface of observation can be treated as the backscattering anomalous electric field $E^{as}(r',\omega)$:

$$E^{as}(r',\omega) = \int \int_S \{j_S^m(r,\omega) \cdot \hat{G}_H^b(r|r',\omega) + j_S^e(r,\omega) \cdot \hat{G}_E^b(r|r',\omega)\} dS =$$

$$\int \int_S n \cdot \{E^{a*}(r,\omega) \times \hat{G}_H^b(r|r',\omega) - H^{a*}(r,\omega) \times \hat{G}_E^b(r|r',\omega)\} dS. \quad (8)$$

Therefore, in accordance with the equations (7) and (8) and the formula $\sigma_a(r') = \sigma_a(r') - i\omega\epsilon_a(r')$, the gradient of the residual field energy flow becomes:

$$\delta\phi(\sigma_b, \sigma_a) =$$

$$-1/2 Re \int \int \int_D \int_\Omega [\sigma_a(r') - i\omega\epsilon_a(r')] E^b(r',\omega) \cdot E^{as}(r',\omega) \, d\omega dv' =$$

$$-1/2 \int \int \int_D \sigma_a(r') A(r') dv' - 1/2 \int \int \int_D \epsilon_a(r') B(r') dv', \quad (9)$$

where A(r) is a cross power spectrum of background and backscattering fields, computed by the formula:

$$A(r) \approx Re \int_{106} E^b(r,\omega) \cdot E^{as}(r,\omega) d\omega, \quad (10)$$

B(r) is a cross power spectrum of the time derivative of the background field and backscattering fields, computed by the formula:

$$B(r) \approx Re \int_{106} (-i\omega) E^b(r,\omega) \cdot E^{as}(r,\omega) d\omega, \quad (11)$$

and $\Omega$ is the frequency range.

Equation (9) provides a choice of selecting $\sigma_a(r')$ minimizing $\Phi$:

$$\sigma_a(r') = \sigma_a(r') - i\omega\epsilon_a(r') = kA(r') - i\omega kB(r'), \quad (12)$$

taking into account, that:

$$\phi(\sigma_b + \sigma_a) = \phi(\sigma_b + kA - i\omega kB) \approx \phi(\sigma_b(r)) + k\delta\phi(\sigma_b, A - i\omega B) =$$

$$\phi(\sigma_b) - 1/2k \int \int \int_D |A(r')|^2 dv' - 1/2k \int \int \int_D |B(r')|^2 dv' < \phi(\tilde{\sigma}_b), \quad (13)$$

where k>0 is a scale factor determined numerically by a linear search for the minimum of the functional:

$$\phi(\sigma_b + \sigma_a) = \phi(\sigma_b + kA - i\omega kB) = \phi(k) = \min. \quad (14)$$

Hence, an important feature of the present invention is the ability to produce anomalous electrical conductivity and dielectric permittivity of the target which minimize the residual field energy flow through the receivers. Generally, this approach is referred to as the inverse problem solution, because the residual field is the difference between the observed data and numerically predicted data, and the goal is to determine the parameters (material properties and location) of the target. The present inventive method resolves this inverse problem in a new way by minimizing residual field energy flow. It is realized numerically through the following three steps:

Step 1. Calculating the background field $\{E^b, H^b\}$ by numerically solving the equations:

$$\nabla \times H^b = \sigma_b E^b + j^e,$$

$$\nabla \times E^b = i\omega\mu H^b, \quad (15)$$

assuming that the sources $j^e$ and background conductivity $\sigma_b$ are known. The numerical methods of solving this problem are well developed. (See Zhdanov, M. S. and G. V. Keller "The geoelectrical methods in geophysical exploration," Elsevier, 1994.) The calculations are simplified in the case of homogeneous or one dimensional background conductivity $\sigma_b$.

Step 2. Calculating the backscattering anomalous field $\{E^{as}, H^{as}\}$ by numerically solving the equations:

$$\nabla \times H^{as} = \sigma_b E^{as} + j_S^e,$$

$$\nabla \times E^{as} = i\omega\mu H^{as} - j_S^m, \quad (16)$$

assuming that the sources $j_S^e$ and $j_S^m$ and background conductivity $\sigma_b$ are known. In particular, equation (16) can be solved using integral formula (8), which actually solves the boundary value problem for backscattering an anomalous field. The numerical methods of calculating electric and magnetic Green's tensors $\hat{G}_E^b$ and $\hat{G}_H^b$ for one dimensional background conductivity $\sigma_b$ (r) are also well developed. (See Zhdanov, M. S., Integral transforms in geophysics, Springer-Verlag, 1988.) In particular, for homogeneous background conductivity, the Green's tensors can be determined by the formulae:

$$\hat{G}_E^b = \left(\hat{I} + \frac{1}{i\omega\mu\tilde{\sigma}_b}\nabla\nabla\right)G^b, \quad \hat{G}_E^b = \frac{1}{i\omega\mu}\nabla\times\hat{I}G^b, \quad (17)$$

where $\hat{I}$ is a unit tensor and $G^b$ b is a scalar Green's function for the Helmholtz equation, calculating by the expression:

$$G^b = G^b(r \mid r', \omega) = -\frac{\exp\left[-(1-i)\sqrt{\omega\mu\tilde{\sigma}_b/2}\,|r-r'|\right]}{4\pi|r-r'|}. \quad (18)$$

Numerical algorithm for backscattering anomalous field reconstruction is given by the formula deriving from equation (8):

$$E^{as}(r',\omega) = \Sigma_{j=1}^N n(r_j) \cdot \{E^a *(r_j,\omega) \times \hat{G}_H^b(r_j|r',\omega) - H^{a*}(r_j,\omega) \times \hat{G}_E^b(r_j|r',\omega)\}\Delta S_j. \quad (19)$$

In the case of transmitters generating a pulse (time domain) background EM field which propagates through the medium containing the object, the calculation of the backscattering field in time domain can be fulfilled by the formula (see Zhdanov, M. S., Integral transforms in geophysics, Springer-Verlag, 1988):

$$E^{as}(r',-t') = \int_T \int_S r' \cdot \{E^a(r,t) \times \hat{G}_H^b(r,t|r',t') - H^a(r,t) \times \hat{G}_E^b(r,t|r',t')\}dSdt. \quad (20)$$

The corresponding numerical formula in time domain has the form:

$$E^{as}(r',-t') = \Sigma_{i=1}^L \Sigma_{j=1}^N n(r_j) \cdot \{E^a(r_j,t_i) \times \hat{G}_H^b(r_j,t_i|r',t') - H^a(r_j,t_i) \times \hat{G}_E^b(r_j,t_i|r',t')\}\Delta S_j \Delta t_i. \quad (21)$$

Step 3. Constructing the volume images of anomalous conductivity $\sigma_a$ and of anomalous permittivity $\epsilon_a$ distributions (the broad band EM holographic images) by calculating cross power spectrum A(r) of background and backscattering fields and cross power spectrum B(r) of the time derivative of the background field and backscattering field:

$$\sigma_a(r) = kA(r) = kRe\Sigma_{m=1}^M E^b(r,\omega_m) \cdot E^{as}(r,\omega_m) \Delta\omega_m, \quad \epsilon_a = kB(r) = kRe\Sigma_{m=1}^M (-i\omega_m)E^b(r,\omega_m) \cdot E^{as}(r,\omega_m) \Delta\omega_m. \quad (22)$$

In the time domain, the calculation of cross power spectra A(r) and B(r) can be reduced to cross correlation between the background and backscattering anomalous fields and between the time derivatives of the background field and the backscattering field:

$$A(r) \approx \int_T E^b(r,t) \cdot E^{as}(r,-t)dt, \quad (23)$$

$$B(r) \approx \int_T \frac{\partial E^b(r,t)}{\partial t} \cdot E^{as}(r,-t)dt.$$

where T is time interval. The last formulae can be computed numerically by the following expressions:

$$A(r) \approx \sum_{l=1}^L E^b(r,t_l) \cdot E^{as}(r,-t_l)\Delta t_l, \quad (24)$$

$$B(r) \approx \sum_{l=1}^L \frac{\partial E^b}{\partial t}(r,t_l) \cdot E^{as}(r,-t_l)\Delta t_l.$$

The volume images of anomalous conductivity $\sigma_a$(r) and of anomalous permittivity $\epsilon_a$(r) are constructed on the basis of cross power spectra A(r) and B(r) by formula (12).

EXAMPLE 3

It is possible to improve the resolution of imaging by repeating the steps of the previous examples iteratively. This procedure solves the inverse problem for determination of the material properties and location of the target.

The general iterative process can be described by the formula:

$$\sigma_{a(n+1)}(r) = \sigma_{a(n)}(r) + k_n A_n(r) - i\omega B_n(r), \quad (25)$$

where n=1,2,3, . . . ,N; $k_l$=k; $A_1(r)$=A(r), $B_1(r)$=B(r); and $\sigma_{a(1)}(r) = \sigma_a(r) - i\omega\epsilon_a(r) = kA(r) - i\omega kB(r)$.

The cross power spectra on the n-th iteration $A_n(r)$ and $B_n(r)$ can be calculated by formulae, analogous to (10) and (11) in the frequency domain:

$$A_n(r) = Re \int \Omega E_n^b(r,\omega) \cdot E_n^a(r,\omega)\,d\omega,$$

$$B_n(r) = Re \int \Omega(-i\omega) E_n^b(r,\omega) \cdot E_n^a(r,\omega)\,d\omega, \quad (26)$$

where $E_n^b(r,\omega)$ is the corrected background field calculated by forward modeling for the geoelectrical model with the corrected background conductivity distribution $\sigma_{b(n)} = \sigma_b + \sigma_{a(n)}$, and $E_n^a(r,\omega)$ is the corrected backscattering field for the corrected residual field $E^{\Delta n}$, which is the difference between the observed field and the corrected background field $E_n^b(r,\omega)$, found on the n-th iteration.

In the time domain, the functions $A_n(r)$ and $B_n(r)$ on the n-th iteration are determined by the cross correlation between corrected background and corrected backscattering fields according to the formulae:

$$A_n(r) = \int_T E_n^b(r,t) \cdot E_n^a(r,-t)dt, \quad (27)$$

$$B_n(r) = \int T \frac{\partial E_n^b(r,t)}{\partial t} \cdot E_n^{as}(r,-t)dt,$$

On every iteration, the same steps are applied:

Step 1. Calculating an updated (corrected) background field as electromagnetic response for the updated background medium with the complex conductivity $\sigma_{b(n)}$(r), obtained on the previous iteration.

Step 2. Calculating the updated residual field between this response and observed field, and then calculating the updated backscattering field for the updated residual field by simulating illumination of the updated background medium with electric and magnetic currents equivalent to those of the updated residual field recorded at the location of the receivers.

Step 3. Constructing the updated volume images of anomalous conductivity $\sigma_{a(n)}$ (r) and of anomalous permittivity $\epsilon_{a(n)}$(r) on the basis of updated [according to the formulae (26) and (27)] cross power spectra $A_n(r)$ and $B_n(r)$ $$\sigma_{a(n)}(r) = k_n A_n(r), \quad \epsilon_{a(n)}(r) = k_n B_n(r) \quad (28)$$

where $k_n > 0$ is a scale factor calculated using the line search for minimum of the energy functional:

$$\Phi(\sigma_{b+\sigma a(n+1)})=\Phi(\sigma_b+\sigma_{a(n)}+k_n A_n - i\omega k_n B_n)=\min. \quad (29)$$

The iterations can be terminated when the functional $\Phi(\sigma_b+\sigma_{(n+1)})$ reaches the required accuracy level.

Thus, the computer of the system may be operated iteratively through the steps of: (1) updating the background field obtained in a previous iteration by adding the volume image constructed during that previous iteration; (2) repeating at least the steps of the method involving measuring (either empirically or numerically) the scattered electromagnetic field with the receivers through obtaining a next generation iteration of a volume image; and (3) repeating steps (1) and (2) until the updated background medium approximates the updated volume image.

Reference in this disclosure to details of specific embodiments is not intended to limit the scope of the appended claims, which themselves recite those features regarded as important to the invention.

INDUSTRIAL APPLICABILITY

The method can be applied in a variety of contexts. For example, internal defects in metal or concrete constructions can be located and imaged. The method is also useful for locating and imaging underground geological structures in connection with exploration for mineral, hydrocarbons and groundwater and in connection with environmental clean up activities. A particularly promising application involves imaging internal structures of living animals, notably the internal organs of the human body. To examine a diseased liver, for example, a normal body may serve as a reference model from which to derive a background field. To examine a diseased bone, such as in the case of osteoporosis, a normal bone may serve as a reference model.

What is claimed is:

1. A method for imaging an anomalous target located in a nontransparent examined medium, said method comprising the steps of:
   a. placing an electromagnetic transmitter source in transmission contact with said examined medium;
   b. placing electromagnetic receivers at various receiving positions with respect to said examined medium, spaced from said transmitter source;
   c. operating said transmitter source to generate a broad band electromagnetic field comprising an harmonic (frequency domain) and/or pulse (time domain) electromagnetic field, whereby said generated electromagnetic field propagates through said examined medium to interact with said target, resulting in a scattered electromagnetic field;
   d. measuring said scattered electromagnetic field with said receivers;
   e. obtaining a background field $\{E^b, H^b\}$ representative of a background medium consisting of said examined medium without the presence of said anomalous target;
   f. obtaining a backscattering anomalous field $\{E^{as}, H^{as}\}$ equivalent to that obtainable by illuminating said background medium with said scattered electromagnetic field transmitted from the positions of said receivers; and
   g. producing a broad band holographic image of said anomalous target by calculating cross power spectra of said background and said backscattering fields or cross correlation functions between said background and said backscattering fields.

2. A method according to claim 1, wherein said transmitter source comprises a plurality of transmitters arranged in an array on the surface of said examined medium.

3. A method according to claim 2, wherein said transmitters include both galvanic and induction transmitters.

4. A method according to claim 1, wherein said receivers include both galvanic and induction receivers.

5. A method according to claim 4, wherein said receivers are arranged in an array on the surface of said examined medium.

6. A method according to claim 1, wherein said scattered electromagnetic field measured by said step d. is input to a computer, and said computer is operated to:
   analyze said scattered electromagnetic field;
   numerically simulate illumination of the background medium by the original transmitter source;
   compute the backscattering anomalous field $\{E^{as}, H^{as}\}$ by simulating illumination of the background medium with electric and magnetic currents equivalent to those of said scattered electromagnetic field transmitted from the locations of said receivers; and
   constructing a volume image of electrical conductivity and/or dielectric permittivity by calculating cross power spectra of said background and backscattering fields.

7. A method according to claim 6, wherein said computer is operated iteratively through the steps of:
   h. updating the background medium of step e. of a previous iteration by adding the volume image constructed by step g. of said previous iteration;
   i. repeating at least steps d through g, whereby to obtain a next generation iteration of a volume image; and
   j. repeating steps h. and i. until said background medium approximates said volume image.

8. A method for imaging an anomalous region located within an organism, said method comprising the steps of:
   a. placing an electromagnetic transmitter source on the surface of said organism;
   b. placing electromagnetic receivers at various positions on the surface of said organism, spaced from said transmitter source;
   c. operating said transmitter source to generate a broad band electromagnetic field comprising an harmonic (frequency domain) and/or pulse (time domain) electromagnetic field, whereby said generated electromagnetic field propagates through said organism to interact with said anomalous region, resulting in a scattered electromagnetic field;
   d. measuring said scattered electromagnetic field with said receivers;
   e. obtaining a background field $\{E^b, H^b\}$ representative of a reference organism equivalent to said organism without the presence of said anomalous region;
   f. obtaining a backscattering anomalous field $\{E^{as}, H^{as}\}$ equivalent to that obtained by illuminating said reference organism by transmitting said scattered electromagnetic field from the positions of said receivers; and
   g. producing a broad band holographic image of said anomalous region by calculating cross power spectra of said background and said backscattering fields or cross correlation functions between said background and said backscattering fields.

\* \* \* \* \*